US012653787B2

(12) United States Patent
Nam et al.

(10) Patent No.: US 12,653,787 B2
(45) Date of Patent: Jun. 16, 2026

(54) PHARMACEUTICAL ORAL DOSAGE FORM OF Q203

(71) Applicant: QURIENT CO., LTD., Gyeonggi-Do (KR)

(72) Inventors: Kiyean Nam, Gyeonggi-Do (KR); Jaeseung Kim, Seoul (KR); Chunwon Jung, Gyeonggi-Do (KR); Saeyeon Lee, Gyeonggi-Do (KR)

(73) Assignee: Qurient Co., Ltd., Gyeonggi-Do (KR)

( * ) Notice: Subject to any disclaimer, the term of this patent is extended or adjusted under 35 U.S.C. 154(b) by 1031 days.

(21) Appl. No.: 17/780,969

(22) PCT Filed: Dec. 17, 2020

(86) PCT No.: PCT/EP2020/086772
§ 371 (c)(1),
(2) Date: May 28, 2022

(87) PCT Pub. No.: WO2021/122996
PCT Pub. Date: Jun. 24, 2021

(65) Prior Publication Data
US 2023/0055208 A1      Feb. 23, 2023

Related U.S. Application Data

(60) Provisional application No. 62/951,393, filed on Dec. 20, 2019.

(51) Int. Cl.
*A61K 9/20*          (2006.01)
*A61K 31/4545*          (2006.01)

(52) U.S. Cl.
CPC .......... *A61K 9/2054* (2013.01); *A61K 9/2009* (2013.01); *A61K 9/2013* (2013.01); *A61K 9/2018* (2013.01); *A61K 9/2027* (2013.01); *A61K 9/2095* (2013.01); *A61K 31/4545* (2013.01)

(58) Field of Classification Search
None
See application file for complete search history.

(56) References Cited

U.S. PATENT DOCUMENTS

| | | | |
|---|---|---|---|
| 8,865,734 B2 | 10/2014 | No et al. | |
| 10,143,657 B2 | 12/2018 | Højgaard | |
| 10,709,699 B2 | 7/2020 | Ding et al. | |
| 2021/0009583 A1* | 1/2021 | Liu ..................... | C07D 471/04 |

FOREIGN PATENT DOCUMENTS

| | | |
|---|---|---|
| WO | 2011113606 A1 | 9/2011 |
| WO | 2014128107 A1 | 8/2014 |
| WO | 2015014993 A2 | 2/2015 |
| WO | 2018158280 A1 | 9/2018 |

OTHER PUBLICATIONS

The Israel Office Action, mailed on Mar. 23, 2025, in the related Israel Patent Application 293888.
The Written Opinion, issued on May 21, 2025, in the related Singapore Appl. No. 11202204437Y.
The International Search Report & Written Opinion, mailed on Apr. 6, 2021, in the related PCT Appl. No. PCT/EP2020/086772.
The Third Party Observation, submitted on Apr. 20, 2022, in the related PCT Appl. No. PCT/EP2020/086772.
The English translation of the Japanese Office Action, mailed on Nov. 12, 2024, in the related Japanese Appl. No. 2022-537481.
The extended European search report, mailed on Oct. 11, 2024, in the related European Appl. No. 24176555.1.
Examination Report No. 1, mailed on Aug. 15, 2025, in the related Australian Patent Application 2020404130.
The Substantive Examination Report, issued on Jul. 28, 2025, in the related Philippine Patent Appl. No. 1-2022-551281.
The English translation of the Chinese Office Action, mailed on Jan. 18, 2024, in the related Chinese Appl. No. 202080085924.X.
Pethe, K., et al. "Discovery of Q203, a potent clinical candidate for the treatment of tuberculosis." Nature medicine 19.9 (2013): pp. 1157-1162.
The English translation of the Chinese Office Action, mailed on Jun. 30, 2023, in the related Chinese Appl. No. 202080085924.X.
Examination Report No. 1, mailed on Oct. 30, 2025, in the related New Zealand Patent Application No. 787615.

* cited by examiner

*Primary Examiner* — Po-Chih Chen

(57) ABSTRACT

The present invention relates to new pharmaceutical dosage forms of 6-chloro-2-ethyl-N-(4-(4-(4-(trifluoromethoxy)phenyl)piperidine-1-yl)benzyl)imidazo[1,2-a]pyridine-3-carboxamide, in particular of its ditosylate form.

24 Claims, 1 Drawing Sheet

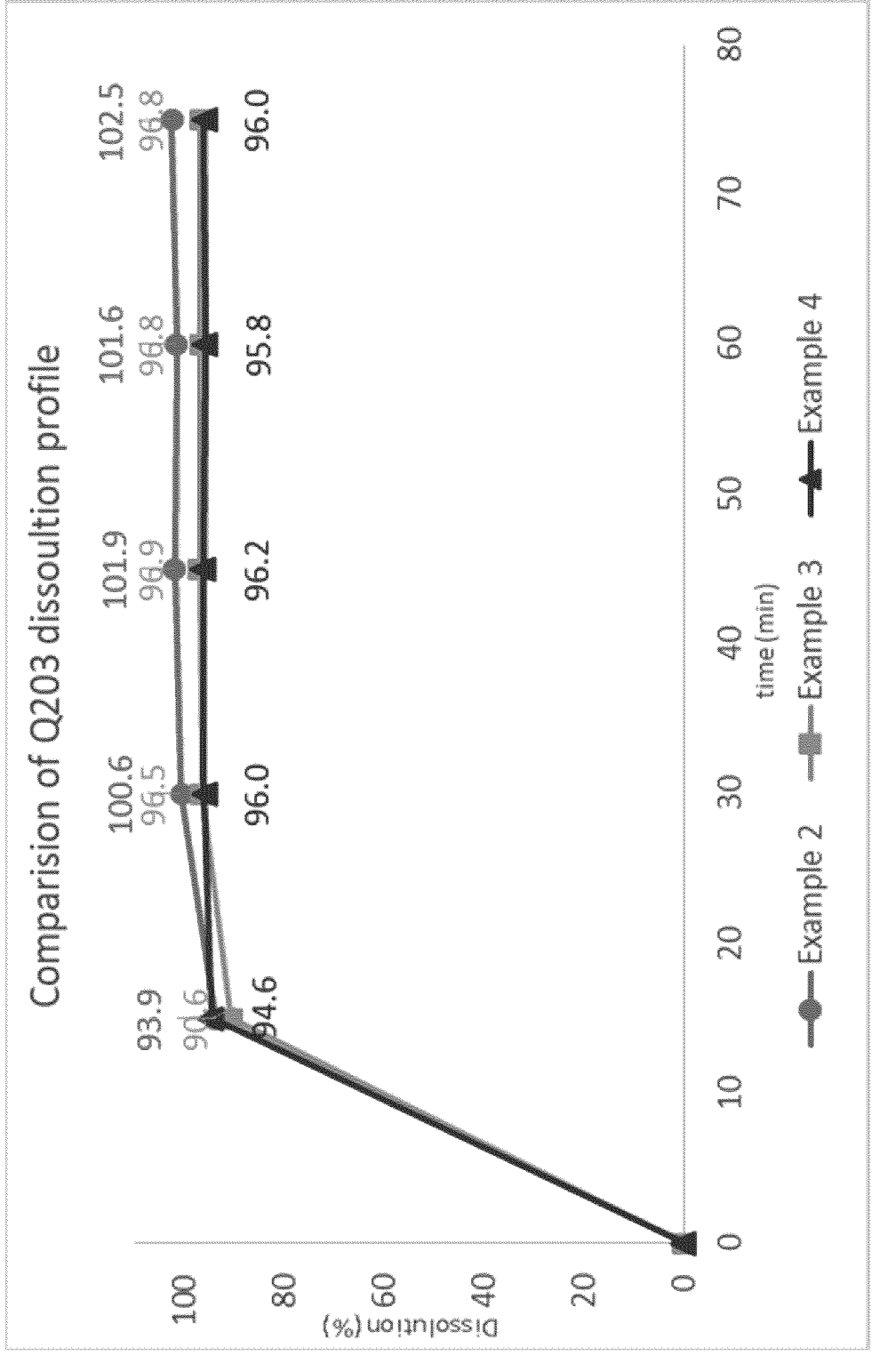

PHARMACEUTICAL ORAL DOSAGE FORM OF Q203

CROSS REFERENCE TO RELATED APPLICATIONS

This application is a National Stage Application of International Application Number PCT/EP2020/086772, filed Dec. 17, 2020; which claims priority to U.S. Provisional Patent Application No. 62/951,393, filed Dec. 20, 2019.

The present invention relates to new pharmaceutical dosage forms of 6-chloro-2-ethyl-N-(4-(4-(4-(trifluoromethoxy)phenyl)piperidine-1-yl)benzyl)imidazo[1,2-a] pyridine-3-carboxamide, in particular of its ditosylate form.

Tuberculosis as a disease continues to result in millions of deaths each year. Inadequate use of chemotherapy has led to an increasing number of drug resistant cases. This situation is likely to worsen with the emergence of extremely resistant strains to all currently known drugs. Current chemotherapy consists of compounds that directly target Mycobacterium tuberculosis, either by neutralizing general information pathways and critical processes such as RNA polymerization and protein synthesis inhibition or by interfering with mycobacterial specific cell envelop synthesis. The most widely used dedicated anti-tubercular drugs isoniazid, ethionamide, and pyriazin amide are pro-drugs that first require activation. They are administered to a patient for a course of several months. Patients infected with multi-drug resistant strains of M. tuberculosis may have to undergo combination therapies for extended periods of time.

WO 2011/113606 describes various anti-tubercular compounds and their use in the treatment of bacterial infections, including compound "Q203" which chemically is 6-chloro-2-ethyl-N-(4-(4-(4-(trifluoromethoxy)phenyl)piperidine-1-yl)benzyl)imidazo[1,2-a]pyridine-3-carboxamide. In a publication by Pethe et al. (Nature Medicine, 19, 1157-1160 (2013), this compound is reported to be active against tuberculosis by interfering with the bacterial energy metabolism, inhibiting cytochrome bc1 activity which is an essential component of the electron transport chain required for synthesis of ATP.

Whilst the compound shows promise for future therapy of tuberculosis and related infections, its administration has been hampered by its rather low solubility in aqueous solutions. This has also made it difficult to manufacture adequate pharmaceutical dosage forms of this compound. Various attempts to formulate this into an appropriate oral dosage form have not been successful.

Accordingly, there is a need in the art to devise and provide a pharmaceutical dosage form that is suitable for oral consumption and that allows the drug to be administered by ingestion.

The present invention addresses these and related needs.

In a first aspect, the present invention relates to a pharmaceutical oral dosage form of 6-chloro-2-ethyl-N-(4-(4-(4-(trifluoromethoxy)phenyl)piperidine-1-yl)benzyl)imidazo[1,2-a]pyridine-3-carboxamide ditosylate, said dosage form comprising a mixture of:

a) granules comprising 6-chloro-2-ethyl-N-(4-(4-(4-(trifluoromethoxy)phenyl)piperidine-1-yl)benzyl)imidazo[1,2-a]pyridine-3-carboxamide ditosylate, at least one intragranular pharmaceutically acceptable excipient, and a solubilizer;

b) a blend surrounding said granules and comprising at least one binder, at least one lubricant and at least one disintegrant, and optionally a filler.

In one embodiment, said at least one intragranular pharmaceutically acceptable excipient is selected from a binder, a filler and a combination of the two.

In one embodiment, said granules (a) consist of 6-chloro-2-ethyl-N-(4-(4-(4-(trifluoromethoxy)phenyl)piperidine-1-yl)benzyl)imidazo[1,2-a]pyridine-3-carboxamide ditosylate, a binder, a filler, and a solubilizer.

In one embodiment, said granules a) do not contain a lubricant and not a disintegrant or superdisintegrant.

In one embodiment, said binder in said granules a) is not: crosslinked starch, microcrystalline cellulose, crosslinked cellulose, crosslinked polyvinylpyrrolidone (crospovidone), crosslinked alginic acid, soy polysaccharide or calcium silicate.

In one embodiment, said binder in said granules a) is selected from acacia gum, gum tragacanth, gelatin, sucrose, starch, and non-crosslinked polyvinyl pyrrolidone (PVP), preferably non-crosslinked polyvinyl pyrrolidone (PVP).

In one embodiment, said binder in said granules a) is present in said pharmaceutical dosage form in an amount of from about 0.1% by weight to 5% by weight, preferably from about 0.2% by weight to 3.5% by weight, more preferably from about 0.3% by weight to 3% by weight.

In one embodiment, said filler in said granules a) is selected from mannitol, dextrose, dextrin, lactose, sorbitol, sucrose, inositol, and is preferably mannitol.

In one embodiment, said filler in said granules a) is present in said pharmaceutical dosage form in an amount of from about 1.5% by weight to 25% by weight, preferably from about 1.75% by weight to 22.5% by weight, more preferably from about 1.9% by weight to 20% by weight.

In one embodiment, said solubilizer in said granules a) is selected from D-α-tocopherol polyethylene glycol succinate (vitamin E-TPGS), sodium lauryl sulphate (SLS), polyoxy ethylene sorbitan monooleate (Tween®), cetyl triamethyl ammonium bromide (CTAB), amino acids such as glycine, polyethylene glycol, and is preferably D-α-tocopherol polyethylene glycol succinate (vitamin E-TPGS).

In one embodiment, said solubilizer in said granules a) is present in said pharmaceutical dosage form in an amount of from about 0.5% by weight to 8% by weight, preferably from about 0.6% by weight to 7.5% by weight, more preferably from about 0.68% by weight to 6.8% by weight.

The pharmaceutical oral dosage form according to any of the foregoing claims, wherein said granules comprise, preferably consist of, 6-chloro-2-ethyl-N-(4-(4-(4-(trifluoromethoxy) phenyl)piperidine-1-yl)benzyl)imidazo[1,2-a]pyridine-3-carboxamide ditosylate, a binder which is non-crosslinked polyvinyl pyrrolidone (PVP), a filler which is mannitol, and a solubilizer which is D-α-tocopherol polyethylene glycol succinate (vitamin E-TPGS).

In one embodiment, said at least one binder in said blend surrounding said granules (b) is selected from starch, microcrystalline cellulose, povidone, hydroxyl propyl cellulose, hydroxyl propyl methyl cellulose and combinations thereof, and is preferably a binder having also a disintegrant quality, and more preferably is microcrystalline cellulose.

In one embodiment, said at least one binder in said blend surrounding said granules (b) is present in said pharmaceutical dosage form in an amount of from about 25% by weight to 50% by weight, preferably from about 28% by weight to 45% by weight, more preferably from about 30% by weight to 43% by weight.

In one embodiment, said at least one lubricant in said blend surrounding said granules (b) is selected from magnesium stearate, calcium stearate, PEG6000, sodium stearyl stearate, sodium lauryl sulphate, colloidal silicon dioxide and combinations thereof, wherein, preferably said at least one lubricant in said blend surrounding said granules (b) is a combination of colloidal silicon dioxide and magnesium stearate.

In one embodiment, said at least one lubricant in said blend surrounding said granules (b) is present in said pharmaceutical dosage form in an amount of from about 1% by weight to 5% by weight, preferably from about 0.5% by weight to 4% by weight, more preferably from about 0.75% by weight to 3.5% by weight, wherein, when said at least one lubricant in said blend surrounding said granules (b) is a combination of colloidal silicon dioxide and magnesium stearate, said colloidal silicon dioxide is present in said pharmaceutical dosage form in an amount of from about 0.5% by weight to 3.5% by weight, preferably from about 1% by weight to 2.5% by weight, more preferably about 2% by weight, and wherein in such combination said magnesium stearate is present in said pharmaceutical dosage form in an amount of from about 0.1% by weight to 2% by weight, preferably from about 0.5% by weight to 1.5% by weight, more preferably about 0.8% by weight.

In one embodiment, said at least one disintegrant in said blend surrounding said granules (b) is selected from cross-linked starch, starch glycolate, e.g. sodium starch glycolate, microcrystalline cellulose, crosslinked cellulose, cross-linked polyvinyl pyrrolidone (crospovidone), crosslinked alginic acid, croscarmellose, e.g. croscarmellose sodium or croscarmellose calcium, soy polysaccharide, and calcium silicate.

In one embodiment, said at least one disintegrant in said blend surrounding said granules (b) is present in said pharmaceutical dosage form in an amount of from about 5% by weight to 12% by weight, preferably from about 7.5% by weight to 10% by weight, more preferably from about 8% by weight to 8.5% by weight.

In one embodiment, said blend surrounding said granules comprises a filler, which preferably is the same filler as the filler comprised in said granules.

In one embodiment, said filler in said blend surrounding said granules is present in said pharmaceutical dosage form in an amount of from about 25% by weight to 50% by weight, preferably from about 27.5% by weight to 45% by weight, more preferably from about 31% by weight to 43% by weight.

In one embodiment, said 6-chloro-2-ethyl-N-(4-(4-(4-(tri-fluoromethoxy)phenyl)piperidine-1-yl)benzyl)imidazo[1,2-a]pyridine-3-carboxamide ditosylate is present in said pharmaceutical dosage form in an amount of from about 1% by weight to 35% by weight, preferably from about 2% by weight to 30% by weight, more preferably from about 2.7% by weight to 27.5% by weight.

In one embodiment, the pharmaceutical oral dosage form comprises a mixture of:

a) granules comprising 6-chloro-2-ethyl-N-(4-(4-(4-(trif-luoromethoxy)phenyl)piperidine-1-yl)benzyl)imidazo[1,2-a]pyridine-3-carboxamide ditosylate in an amount of about 23-30% by weight of the dosage form, mannitol in an amount of about 15-25% by weight of the dosage form, polyvinylpyrrolidone in an amount of about 1-5% by weight of the dosage form, D-α-tocopherol polyethylene glycol succinate (vitamin E-TPGS) in an amount of about 5-8% by weight of the dosage form; and b) blend surrounding said granules surrounding said gran-ules and comprising microcrystalline cellulose in an amount of about 30-34% by weight of the dosage form, colloidal silicon dioxide in an amount of about 1-3% by weight of the dosage form, magnesium stearate in an amount of about 0.5-1.5% by weight of the dosage form, and croscarmellose sodium in an amount of about 7-10% by weight of the dosage form;
or c) granules comprising 6-chloro-2-ethyl-N-(4-(4-(4-(trif-luoromethoxy)phenyl)piperidine-1-yl)benzyl)imidazo[1,2-a]pyridine-3-carboxamide ditosylate in an amount of about 12-15% by weight of the dosage form, man-nitol in an amount of about 8-12% by weight of the dosage form, polyvinylpyrrolidone in an amount of 1-2% by weight of the dosage form, D-α-tocopherol polyethylene glycol succinate (vitamin E-TPGS) in an amount of about 2-5% by weight of the dosage form; and d) blend surrounding said granules surrounding said gran-ules and comprising microcrystalline cellulose in an amount of about 30-33% by weight of the dosage form, mannitol in an amount of about 30-33% by weight of the dosage form, magnesium stearate in an amount of about 0.5-1.5% by weight of the dosage form, and croscarmellose sodium in an amount of about 7-10% by weight of the dosage form;
or e) granules comprising 6-chloro-2-ethyl-N-(4-(4-(4-(trif-luoromethoxy)phenyl)piperidine-1-yl)benzyl)imidazo[1,2-a]pyridine-3-carboxamide ditosylate in an amount of about 1-5% by weight of the dosage form, mannitol in an amount of about 1-3% by weight of the dosage form, polyvinylpyrrolidone in an amount of about 0.1-0.5% by weight of the dosage form, D-α-tocoph-erol polyethylene glycol succinate (vitamin E-TPGS) in an amount of about 0.5-0.8% by weight of the dosage form; and f) blend surrounding said granules surrounding said gran-ules and comprising microcrystalline cellulose in an amount of about 40-45% by weight of the dosage form, mannitol in an amount of about 40-45% by weight of the dosage form, magnesium stearate in an amount of about 0.5-1.5% by weight of the dosage form, and croscarmellose sodium in an amount of about 7-10% by weight of the dosage form.

In a further aspect, the present invention relates to a process for preparing a pharmaceutical oral dosage form as defined above, wherein said process comprises:

i. Granulating 6-chloro-2-ethyl-N-(4-(4-(4-(trifluo-romethoxy)phenyl)piperidine-1-yl)benzyl)imidazo[1,2-a]pyridine-3-carboxamide ditosylate and the compo-nents of said granules a), as defined above, by a suitable granulation process; said
suitable granulation process preferably being selected from fluid bed granulation, high shear granulation, fluid bed drying, fluidized spray drying, single pot granulation, steam granulation, thermal adhesion granulation, pneumatic dry granulation, moisture activated dry granulation, melt granulation, freeze granulation, and foam granulation;

ii. Blending the granules obtained in step i. with the components of said blend, as defined above;

iii. Compressing the mixture obtained in step ii. into a pharmaceutical dosage form, preferably a tablet; and, optionally iv. Coating the dosage form obtained in step iii.

In yet a further aspect, the present invention relates to a pharmaceutical oral dosage form obtainable by a process as defined above.

In still another aspect the present invention relates to a pharmaceutical oral dosage form according to the present invention for use in the treatment of a bacterial infection, preferably tuberculosis or Buruli ulcer.

In yet a further aspect, the present invention also relates to a method of treatment of a bacterial infection, preferably tuberculosis or Buruli ulcer, wherein said pharmaceutical dosage form is administered to a patient in need thereof.

The present inventors have surprisingly found that it is possible to formulate 6-chloro-2-ethyl-N-(4-(4-(4-(trifluoromethoxy)phenyl)piperidin-1-yl)benzyl)imidazo[1,2-a]pyridine-3-carboxamide ditosylate (Q203) into a pharmaceutical oral dosage form. This dosage form can be produced by a robust manufacturing process which provides high uniformity of dosage. Moreover, the pharmaceutical dosage form in accordance with embodiments of the invention can be designed to achieve a highly reproducible disintegration and/or dissolution in aqueous solutions.

The invention is now further described by reference to the following FIGURE which is given to illustrate, not to limit the present invention.

More specifically,

FIG. 1 shows a comparison of Q203 dissolution profiles of various tablet formulations shown hereafter.

The invention is now further described by reference to the following examples which are given to illustrate, not to limit the present invention.

EXAMPLES

An exemplary formulation containing Q203 as active ingredient was manufactured. In order to confirm the manufacturability of samples for veriour strengths, low, mid and high concentration of Q203 tablets were produced and were prepared as following general procedure: granulation, blending, compression and coating.

Example 1

Composition of Formulation

| Ingredients | % Level |
| --- | --- |
| Q203 | 28.1 |
| Mannitol | 20.7 |
| Microcrystalline Cellulose | 25.7 |
| Croscarmellose Sodium | 3.4 |
| PVP K29/32 | 4.3 |
| Colloidal Silicon Dioxide | 1.4 |
| Vitamin E TPGS | 7.1 |
| Croscarmellose Sodium | 8.4 |
| Magnesium Stearate | 0.9 |
| Total: | 100 |

Process of Formulation Preparation

1. Screen Q203, Minntol, Microcrystalline Cellulose, Croscarmellose Sodium, Colloidal Silicon Dioxide and PVP K29/32.
2. Add #1 powder into granulator and mix.
3. Add vitamin E-TPGS in water.
4. Mix and dry.
5. Discharge and screen granules
6. Load the blender with the granules, Colloidal Silicon Dioxide, Croscarmellose Sodium, and Magnesium Stearate.

7. Blend for more than 15 minutes.
8. Discharge and compress tablets.

Example 2

Composition of Formulation

| Ingredients | % Level |
| --- | --- |
| Q203 | 28.1 |
| Mannitol | 20.7 |
| Microcrystalline Cellulose | 12.8 |
| Croscarmellose Sodium | 3.4 |
| PVP K29/32 | 4.3 |
| Colloidal Silicon Dioxide | 1.4 |
| Vitamin E TPGS | 7.1 |
| Microcrystalline Cellulose | 12.9 |
| Croscarmellose Sodium | 8.4 |
| Magnesium Stearate | 0.9 |
| Total: | 100 |

Process of Formulation Preparation

1. Screen Q203, Minntol, Microcrystalline Cellulose, Croscarmellose Sodium, Colloidal Silicon Dioxide and PVP K29/32.
2. Add #1 powder into granulator and mix.
3. Add vitamin E-TPGS in water.
4. Mix and dry.
5. Discharge and screen granules
6. Load the blender with the granules, Microcrystalline Cellulose, Colloidal Silicon Dioxide, Croscarmellose Sodium, and Magnesium Stearate.
7. Blend for more than 15 minutes.
8. Discharge and compress tablets.

Example 3

Composition of Formulation

| Ingredients | % Level |
| --- | --- |
| Q203 | 13.6% |
| Mannitol | 10.0% |
| PVP K29/32 | 1.5% |
| Vitamin E TPGS | 3.4 |
| Microcrystalline Cellulose | 31.3 |
| Mannitol | 31.3 |
| Croscarmellose Sodium | 8.2 |
| Magnesium Stearate | 0.8 |
| Total: | 100 |

Process of Formulation Preparation

1. Screen Q203, Minntol and PVP K29/32.
2. Add #1 powder into granulator and mix.
3. Add vitamin E-TPGS in water.
4. Mix and dry.
5. Discharge and screen granules
6. Load the blender with the granules, Microcrystalline Cellulose, Mannitol, Croscarmellose Sodium and Magnesium stearate.
7. Blend for more than 15 minutes.
8. Discharge and compress tablets.

Example 4

Composition of Formulation

| Ingredients | % Level |
|---|---|
| Q203 | 2.8 |
| Mannitol | 2.1 |
| Microcrystalline Cellulose | 1.3 |
| Croscarmellose Sodium | 0.3 |
| PVP K29/32 | 0.4 |
| Colloidal Silicon Dioxide | 0.1 |
| Vitamin E TPGS | 0.7 |
| Mannitol | 41.3 |
| Microcrystalline Cellulose | 41.3 |
| Croscarmellose Sodium | 8.4 |
| Magnesium Stearate | 1.2 |
| Total: | 100 |

Process of Formulation Preparation
1. Screen Q203, Minntol, Microcrystalline Cellulose, Croscarmellose Sodium, Colloidal Silicon Dioxide and PVP K29/32.
2. Add #1 powder into granulator and mix.
3. Add vitamin E-TPGS in water.
4. Mix and dry.
5. Discharge and screen granules
6. Load the blender with the granules, Mannitol, Microcrystalline Cellulose, Croscarmellose Sodium and Magnesium Stearate.
7. Blend for more than 15 minutes.
8. Discharge and compress tablets.

Example 5

Comparison of Q203 Dissolution Profiles

A drug-release test which utilizes the USP Apparatus 2 at 75 rpm with 900 mL of 0.1N HCl, was used to study the in vitro release at 37° C.±0.5° C. In the guidance about dissolution testing of immediate release solid oral dosage forms, for BCS class 2 products which are slowly dissolving or poorly water soluble drugs, it was recommended to characterize the quality of the product to ensure 85% dissolution. Manufactured Q203 tablets in accordance with examples 2, 3 and 4 showed to dissolve quickly; and complete dissolution (>90%) at 15 min is observed for all three batches. So those formulation are appropriate formulations and achieve a highly reproducible disintegration and/or dissolution. Results are shown in the following table and in FIG. 1. (It should be noted that a dissolution >100% means that such dissolution is higher than the dissolution of the respective control formulation used in the dissolution test.)

| Time (min) | Example 2 [% dissolution] | Example 3 [% dissolution] | Example 4 [% dissolution] |
|---|---|---|---|
| 0 | 0 | 0 | 0 |
| 15 | 93.9 | 90.6 | 94.6 |
| 30 | 100.6 | 96.5 | 96 |
| 45 | 101.9 | 96.9 | 96.2 |
| 60 | 101.6 | 96.8 | 95.8 |
| 75 | 102.5 | 96.8 | 96 |

The invention claimed is:
1. A pharmaceutical oral dosage form of 6-chloro-2-ethyl-N-(4-(4-(4-(trifluoromethoxy)phenyl)piperidine-1-yl)benzyl)imidazo[1,2-a]pyridine-3-carboxamide ditosylate, said dosage form comprising a mixture of:
   a) granules comprising 6-chloro-2-ethyl-N-(4-(4-(4-(trifluoromethoxy)phenyl) piperidine-1-yl)benzyl)imidazo [1,2-a]pyridine-3-carboxamide ditosylate, at least one intragranular pharmaceutically acceptable excipient, and a solubilizer; and
   b) a blend surrounding said granules and comprising at least one binder, at least one lubricant and at least one disintegrant, and optionally a filler.
2. The pharmaceutical oral dosage form according to claim 1, wherein said at least one intragranular pharmaceutically acceptable excipient is selected from a binder, a filler and a combination of the binder and filler.
3. The pharmaceutical oral dosage form according to claim 1, wherein said granules a) consist of 6-chloro-2-ethyl-N-(4-(4-(4-(trifluoromethoxy)phenyl)piperidine-1-yl)benzyl)imidazo[1,2-a]pyridine-3-carboxamide ditosylate, a binder, a filler, and a solubilizer.
4. The pharmaceutical oral dosage form according to claim 1,
   wherein said granules a) do not contain a lubricant and not a disintegrant or superdisintegrant.
5. The pharmaceutical oral dosage form according to claim 2, wherein said binder in said granules a) is not: crosslinked starch, microcrystalline cellulose, crosslinked cellulose, crosslinked polyvinylpyrrolidone, crosslinked alginic acid, soy polysaccharide or calcium silicate.
6. The pharmaceutical oral dosage form according to claim 2, wherein said binder in said granules a) is selected from acacia gum, gum tragacanth, gelatin, sucrose, starch, and non-crosslinked polyvinylpyrrolidone (PVP).
7. The pharmaceutical oral dosage form according to claim 6, wherein said binder in said granules a) is present in said pharmaceutical dosage form in an amount of from about 0.1% by weight to 5% by weight.
8. The pharmaceutical oral dosage form according to claim 2, wherein said filler in said granules a) is selected from mannitol, dextrose, dextrin, lactose, sorbitol, sucrose, and inositol.
9. The pharmaceutical oral dosage form according to claim 8, wherein said filler in said granules a) is present in said pharmaceutical dosage form in an amount of from about 1.5% by weight to 25% by weight.
10. The pharmaceutical oral dosage form according to claim 1, wherein said solubilizer in said granules a) is selected from D-α-tocopherol polyethylene glycol succinate (vitamin E-TPGS), sodium lauryl sulphate (SLS), polyoxyethylene sorbitan monooleate, cetyltriamethylammonium bromide (CTAB), amino acids, and polyethylene glycol.
11. The pharmaceutical oral dosage form according to claim 10, wherein said solubilizer in said granules a) is present in said pharmaceutical dosage form in an amount of from about 0.5% by weight to 8% by weight.
12. The pharmaceutical oral dosage form according to claim 1, wherein said granules consist of, 6-chloro-2-ethyl-N-(4-(4-(4-(trifluoromethoxy)phenyl)piperidine-1-yl)benzyl)imidazo[1,2-a]pyridine-3-carboxamide ditosylate, a binder which is non-crosslinked polyvinylpyrrolidone (PVP), a filler which is mannitol, and a solubilizer which is D-α-tocopherol polyethylene glycol succinate (vitamin E-TPGS).
13. The pharmaceutical oral dosage form according to claim 1, wherein said at least one binder in said blend surrounding said granules b) is selected from starch, microcrystalline cellulose, povidone, hydroxypropyl cellulose, hydroxypropylmethyl cellulose and combinations thereof.

14. The pharmaceutical oral dosage form according to claim 13, wherein said at least one binder in said blend surrounding said granules b) is present in said pharmaceutical dosage form in an amount of from about 25% by weight to 50% by weight.

15. The pharmaceutical oral dosage form according to claim 1, wherein said at least one lubricant in said blend surrounding said granules b) is selected from magnesium stearate, calcium stearate, PEG6000, sodium stearyl stearate, sodium lauryl sulphate, colloidal silicon dioxide and combinations thereof.

16. The pharmaceutical oral dosage form according to claim 15, wherein said at least one lubricant in said blend surrounding said granules b) is present in said pharmaceutical dosage form in an amount of from about 1% by weight to 5% by weight, wherein, when said at least one lubricant in said blend surrounding said granules b) is a combination of colloidal silicon dioxide and magnesium stearate, said colloidal silicon dioxide is present in said pharmaceutical dosage form in an amount of from about 0.5% by weight to 3.5% by weight, and wherein in such combination said magnesium stearate is present in said pharmaceutical dosage form in an amount of from about 0.1% by weight to 2% by weight.

17. The pharmaceutical oral dosage form according to claim 1, wherein said at least one disintegrant in said blend surrounding said granules b) is selected from crosslinked starch, starch glycolate, microcrystalline cellulose, crosslinked cellulose, crosslinked polyvinylpyrrolidone, crosslinked alginic acid, croscarmellose, soy polysaccharide, and calcium silicate.

18. The pharmaceutical oral dosage form according to claim 17, wherein said at least one disintegrant in said blend surrounding said granules b) is present in said pharmaceutical dosage form in an amount of from about 5% by weight to 12% by weight.

19. The pharmaceutical oral dosage form according to claim 2, wherein said blend surrounding said granules comprises a filler, which is the same filler as the filler in said granules.

20. The pharmaceutical oral dosage form according to claim 19, wherein said filler in said blend surrounding said granules is present in said pharmaceutical dosage form in an amount of from about 25% by weight to 50% by weight.

21. The pharmaceutical oral dosage form according to claim 1, wherein said 6-chloro-2-ethyl-N-(4-(4-(4-(trifluoromethoxy)phenyl)piperidine-1-yl)benzyl)imidazo[1,2-a]pyridine-3-carboxamide ditosylate is present in said pharmaceutical dosage form in an amount of from about 1% by weight to 35% by weight.

22. The pharmaceutical oral dosage form according to claim 1, comprising a mixture of:
   a) granules comprising 6-chloro-2-ethyl-N-(4-(4-(4-(trifluoromethoxy)phenyl) piperidine-1-yl)benzyl)imidazo[1,2-a]pyridine-3-carboxamide ditosylate in an amount of about 23-30% by weight of the dosage form, mannitol in an amount of about 15-25% by weight of the dosage form, polyvinylpyrrolidone in an amount of about 1-5% by weight of the dosage form, D-α-tocopherol polyethylene glycol succinate (vitamin E-TPGS) in an amount of about 5-8% by weight of the dosage form; and
   b) a blend surrounding said granules and comprising microcrystalline cellulose in an amount of about 30-34% by weight of the dosage form, colloidal silicon dioxide in an amount of about 1-3% by weight of the dosage form, magnesium stearate in an amount of about 0.5-1.5% by weight of the dosage form, and croscarmellose sodium in an amount of about 7-10% by weight of the dosage form; or
   c) granules comprising 6-chloro-2-ethyl-N-(4-(4-(4-(trifluoromethoxy)phenyl) piperidine-1-yl)benzyl)imidazo[1,2-a]pyridine-3-carboxamide ditosylate in an amount of about 12-15% by weight of the dosage form, mannitol in an amount of about 8-12% by weight of the dosage form, polyvinylpyrrolidone in an amount of 1-2% by weight of the dosage form, D-α-tocopherol polyethylene glycol succinate (vitamin E-TPGS) in an amount of about 2-5% by weight of the dosage form; and
   d) a blend surrounding said granules and comprising microcrystalline cellulose in an amount of about 30-33% by weight of the dosage form, mannitol in an amount of about 30-33% by weight of the dosage form, magnesium stearate in an amount of about 0.5-1.5% by weight of the dosage form, and croscarmellose sodium in an amount of about 7-10% by weight of the dosage form; or
   e) granules comprising 6-chloro-2-ethyl-N-(4-(4-(4-(trifluoromethoxy)phenyl) piperidine-1-yl)benzyl)imidazo[1,2-a]pyridine-3-carboxamide ditosylate in an amount of about 1-5% by weight of the dosage form, mannitol in an amount of about 1-3% by weight of the dosage form, polyvinylpyrrolidone in an amount of about 0.1-0.5% by weight of the dosage form, D-α-tocopherol polyethylene glycol succinate (vitamin E-TPGS) in an amount of about 0.5-0.8% by weight of the dosage form; and
   f) a blend surrounding said granules and comprising microcrystalline cellulose in an amount of about 40-45% by weight of the dosage form, mannitol in an amount of about 40-45% by weight of the dosage form, magnesium stearate in an amount of about 0.5-1.5% by weight of the dosage form, and croscarmellose sodium in an amount of about 7-10% by weight of the dosage form.

23. A process for preparing a pharmaceutical oral dosage form as defined in claim 1, wherein said process comprises:
   i) granulating 6-chloro-2-ethyl-N-(4-(4-(4-(trifluoromethoxy)phenyl)piperidine-1-yl)benzyl)imidazo[1,2-a]pyridine-3-carboxamide ditosylate and components of said granules a), as defined in claim 1, by a suitable granulation process;
   ii) blending the granules obtained in step i) with components of said blend, as defined in claim 1;
   iii) compressing mixture obtained in step ii) into a pharmaceutical dosage form; and, optionally
   iv) coating the dosage form obtained in step iii).

24. A method for the treatment of a bacterial infection wherein said treatment comprises administering, to a subject with the infection, a pharmaceutical oral dosage form according to claim 1.

* * * * *